(12) United States Patent
Kon et al.

(10) Patent No.: US 8,309,762 B2
(45) Date of Patent: Nov. 13, 2012

(54) METHOD FOR PRODUCING CARBOXYLIC ACID

(75) Inventors: Yoshihiro Kon, Tsukuba (JP); Kazuhiko Sato, Tsukuba (JP); Hideaki Yazawa, Iwaki (JP); Chikara Ohto, Toyota (JP); Yukio Okamura, Nagoya (JP)

(73) Assignee: Toyota Jidosha Kabushiki Kaisha, Aichi (JP)

( * ) Notice: Subject to any disclaimer, the term of this patent is extended or adjusted under 35 U.S.C. 154(b) by 138 days.

(21) Appl. No.: 12/698,442

(22) Filed: Feb. 2, 2010

(65) Prior Publication Data

US 2010/0210873 A1 Aug. 19, 2010

(30) Foreign Application Priority Data

Feb. 18, 2009 (JP) ................. 2009-035529

(51) Int. Cl.
*C07C 51/16* (2006.01)
*C07C 55/00* (2006.01)
(52) U.S. Cl. ...................... 562/524; 562/512.4; 562/590
(58) Field of Classification Search ........................ None
See application file for complete search history.

(56) References Cited

U.S. PATENT DOCUMENTS

| 4,532,079 | A | 7/1985 | Venturello et al. |
| 5,596,111 | A | 1/1997 | Sibi et al. |

FOREIGN PATENT DOCUMENTS

| JP | 60-034929 A | 2/1985 |
| JP | 63-093746 A | 4/1988 |
| JP | 05-004938 A | 1/1993 |
| JP | 2000-086574 A | 3/2000 |
| JP | 2008-156298 A | 7/2008 |
| JP | 2008156298 | * 7/2008 |

OTHER PUBLICATIONS

Machine translation of JP 2008156298.*

* cited by examiner

*Primary Examiner* — Karl J Puttlitz
(74) *Attorney, Agent, or Firm* — Sughrue Mion, PLLC

(57) ABSTRACT

It is an object of this invention to provide a method for efficiently synthesizing monocarboxylic acid, dicarboxylic acid, and tricarboxylic acid with the use of unsaturated triacyl glycerol as a starting material and hydrogen peroxide as an oxidant. Such method comprises allowing unsaturated triacyl glycerol to react with hydrogen peroxide in the presence of a quaternary ammonium polybasic acid hydrogen salt and at least one member selected from the group consisting of tungstic acid, heterotungstic acid, and salts thereof.

7 Claims, No Drawings

METHOD FOR PRODUCING CARBOXYLIC ACID

BACKGROUND OF THE INVENTION

1. Field of the Invention

The present invention relates to a method for producing carboxylic acid. More specifically, the present invention relates to a method for producing carboxylic acid that is useful as a polyester-based plasticizer or the like.

2. Background Art

Carboxylic acid is a useful substance that has been widely used as a starting material for polyester-based plasticizers, nylons, polyester materials, lubricating oil, and the like. There are a variety of known production methods thereof. In general, alcohol or aldehyde oxidation with the use of a metal compound such as potassium permanganate or potassium dichromate and oxidative cleavage of olefins with the use of an oxidant such as ozone have been conducted. However, since toxic substances such as metal compounds and ozone are handled when using such methods, there are still many problematic issues regarding industrial-scale production. In addition, in the case of a method using a metal compound, a large amount of waste containing heavy metals is generated due to poor selectivity, which is problematic. Further, in the case of a method using ozone, high electrical power is necessary for synthesizing a large amount of ozone. Therefore, the method is inappropriate for bioplastic material synthesis technology that contributes to the resolution of environmental problems.

Therefore, a recently known method for producing carboxylic acid is a method for producing carboxylic acid involving oxidative cleavage with the use of an oxidant such as hydrogen peroxide. For instance, JP Patent Publication (Kokai) No. 60-34929 A (1985) discloses a method for obtaining azelaic acid and pelargonic acid by allowing oleic acid to react with hydrogen peroxide with the use of a complex compound of phosphotungstic acid and quaternary amine as a catalyst. In addition, JP Patent Publication (Kokai) No. 63-93746 A (1988) discloses a method for producing azelaic acid and pelargonic acid from oleic acid as in the above case with the use of heteropoly acid as a catalyst. However, in terms of industrial practice, these methods are disadvantageous, for example, in that they require complicated operations, and in that the production cost is high.

Further, JP Patent Publication (Kokai) No. 5-4938 A (1993) discloses that saturated carboxylic acid can be obtained at a good yield through simple production steps even with the use of low-concentration hydrogen peroxide by carrying out an oxidative cleavage reaction for oxidation of unsaturated carboxylic acid with hydrogen peroxide, provided that tungstic acid, phosphotungstic acid, or the like and a quaternary amine salt are separately added to the reaction system.

The above conventional techniques are insufficient for practical use due to, for example, the following reasons: dicarboxylic acid cannot be synthesized directly from a starting material which is a plant seed oil such as triolein or plant oil such as canola oil or carrot oil; and tricarboxylic acid has not been successfully synthesized. Tricarboxylic acid is a trifunctional monomer and is useful as a crosslinking agent for bioplastics. However, it has been difficult to produce tricarboxylic acid by conventional synthesis methods involving the use of petroleum as a starting material.

SUMMARY OF THE INVENTION

In view of the above, it is an object of the present invention to provide a method for efficiently synthesizing monocarboxylic acid, dicarboxylic acid, and tricarboxylic acid with the use of unsaturated triacyl glycerol as a starting material and hydrogen peroxide as an oxidant.

The present inventors have found that tricarboxylic acid such as triazelaic acid can be generated when unsaturated triacyl glycerol is allowed to react with hydrogen peroxide with the use of tungstic acids and a quaternary ammonium polybasic acid hydrogen salt as a catalyst. This has led to the completion of the present invention.

Specifically, the summary of the present invention is described as follows.

(1) A method for producing carboxylic acid, comprising allowing unsaturated triacyl glycerol to react with hydrogen peroxide in the presence of a quaternary ammonium polybasic acid hydrogen salt and at least one member selected from the group consisting of tungstic acid, heterotungstic acid, and salts thereof.

(2) The method for producing carboxylic acid according to (1), wherein unsaturated triacyl glycerol is triolein or carrot oil.

(3) The method for producing carboxylic acid according to (1) or (2), wherein at least one member selected from the group consisting of tungstic acid, heterotungstic acid, and salts thereof is sodium tungstate.

(4) The method for producing carboxylic acid according to (1) or (2), wherein at least one member selected from the group consisting of tungstic acid, heterotungstic acid, and salts thereof is phosphosodium tungstate.

(5) The method for producing carboxylic acid according to any one of (1) to (4), wherein the quaternary ammonium polybasic acid hydrogen salt is hydrogen sulfate methyltrioctyl ammonium.

(6) The method for producing carboxylic acid according to any one of (1) to (5), wherein carboxylic acid is at least one member selected from the group consisting of monocarboxylic acid, dicarboxylic acid, and tricarboxylic acid.

Effects of the Invention

According to the present invention, polycarboxylic acid such as dicarboxylic acid or tricarboxylic acid can be efficiently obtained via oxidative degradation of a C=C double bond of unsaturated triacyl glycerol in a specific manner with the use of hydrogen peroxide as an oxidant. In such case, the reaction efficiency reaches a level of 2 to 5 times as great as that in the case of a conventional method. In addition, obtained tricarboxylic acid can be preferably used for a crosslinking agent and the like for bioplastics.

In addition, the present invention can be carried out without using halogen or causing the generation of harmful waste. Further, in a case in which sodium tungstate is used, the amount of a tungsten element can be reduced to approximately $1/12$ that of phosphotungstic acid used in a conventional method.

This application claims priority to JP Application No. 2009-035529, of which the contents of the specifications are herein incorporated by reference in their entirety.

EMBODIMENTS FOR CARRYING OUT THE INVENTION

Hereafter, the present invention is described in detail.

The method for producing carboxylic acid of the present invention comprises allowing unsaturated triacyl glycerol to react with hydrogen peroxide in the presence of a quaternary ammonium polybasic acid hydrogen salt and at least one member selected from the group consisting of tungstic acid, heterotungstic acid, and salts thereof.

Unsaturated triacyl glycerol used in the present invention as a starting material is glycerol (glycerin) having three fatty acid molecules bound thereto via an ester bond. Fatty acid is not particularly limited as long as it is unsaturated fatty acid having at least one intramolecular double bond. Monovalent unsaturated fatty acid, polyunsaturated fatty acid, single-chain unsaturated fatty acid, and branched unsaturated fatty acid can be used. In addition, either cis-type unsaturated fatty acid or trans-type unsaturated fatty acid may be used. The carbon number of a fatty acid portion is not particularly limited. However, it is preferably 8 to 26 and more preferably 16 to 22.

Examples of unsaturated fatty acid include oleic acid, palmitoleic acid, petroselinic acid, erucic acid, brassidic acid, obtusilic acid, caprenic acid, undecylenic acid, linderic acid, tsuzuic acid, physeteric acid, myristoleic acid, elaidic acid, asclepinic acid, vaccenic acid, gadoleic acid, gondoic acid, cetoleic acid, and cis-6-hexadecenoic acid. In the case of petroselinic acid, dicarboxylic acid generated by the present invention results in adipic acid used for synthesis of nylon and the like, which is industrially useful.

Examples of polyunsaturated fatty acid include linoleic acid, linolenic acid, γ-linolenic acid, ricinoleic acid, α-eleostearic acid, β-eleostearic acid, punica acid, trans-10-octadecadienoic acid, and trans-12-octadecadienoic acid.

In the method of the present invention, one type of glycerol ester comprising glycerol having any one of the above unsaturated fatty acids bound thereto may be used. Alternatively, a mixture of two or more types of glycerol esters each comprising glycerol having a different unsaturated fatty acid bound thereto may be used. It is also possible to use plant oil or plant fat and oil containing the above unsaturated triacyl glycerol. Specific examples thereof include plant seed-derived triolein (trioleic glycerol), carrot oil, and canola oil. Herein, carrot oil mainly contains three different unsaturated triacyl glycerols to which petroselinic acid, oleic acid, and linoleic acid have separately been bound.

Examples of tungstic acid used as a metal catalyst include $H_2W_2O_7$ and $H_2WO_4$. Examples of salts thereof include alkali metal salts such as lithium salt, sodium salt, and potassium salt. Of these, sodium tungstate ($Na_2WO_4$) is particularly preferably used.

In addition, heterotungstic acid is obtained by inserting a heteroatom of phosphorus, silicon, or the like into the tungstic acid backbone. Examples thereof include silicon tungstate ($H_3(SiW_{12}O_{40}).nH_2O$) and phosphotungstic acid ($H_3(PW_{12}O_{40}).nH_2O$). Examples of salts thereof include alkali metal salts such as lithium salts, sodium salts, and potassium salts. Particularly preferably, phosphosodium tungstate ($Na(PW_{12}O_{40}).nH_2O$) is used. The number of crystallization water molecules is not particularly limited. In general, it is 20 to 40.

Among tungstic acid, heterotungstic acid, and salts thereof described above, one member may be used or a plurality of members may be used in combination.

The term "quaternary ammonium polybasic acid hydrogen salt" used in the present invention refers to an ammonium salt represented by the following formula:

(wherein each of $R^1$, $R^2$, $R^3$ and $R^4$ independently represents a $C_1$-$C_{10}$ alkyl or aralkyl group and $X^-$ represents a polybasic acid hydrogen ion).

Examples of $C_1$-$C_{10}$ alkyl groups include methyl, ethyl, propyl, butyl, pentyl, hexyl, heptyl, and octyl groups. In addition, examples of aralkyl groups include a benzyl group.

Examples of quaternary ammonium ions represented by $[R^1R^2R^3R^4N]^+$ include a trioctylmethylammonium ion, a tetrabutylammonium ion, and a benzyltriethylammonium ion.

In addition, examples of polybasic acid hydrogen ions represented by $X^-$ include a hydrogen sulfate ion, a hydrogen carbonate ion, a hydrogen phosphate ion, a hydrogen arsenate ion, and a hydrogen selenate ion. A particularly preferable quaternary ammonium polybasic acid hydrogen salt is hydrogen sulfate methyltrioctyl ammonium. In addition, any example of a quaternary ammonium polybasic acid hydrogen salt described above may be used alone, or different examples thereof may be used in combination.

For example, hydrogen peroxide may be used in the form of an aqueous solution (i.e., hydrogen peroxide water). The concentration of hydrogen peroxide used in the form of an aqueous solution is not particularly limited. However, according to studies conducted by the present inventors, an oxidation reaction efficiently proceeds even with the use of low-concentration hydrogen peroxide water (e.g., 1 to 30 wt %) in the presence of tungstic acid, heterotungstic acid, a salt of either thereof, and a quaternary ammonium polybasic acid hydrogen salt. In conventional methods, high-concentration hydrogen peroxide water (e.g., 65 wt %) is necessary for sufficient exertion of catalyst activity. However, according to the method of the present invention, low-concentration hydrogen peroxide can be used. Therefore, the method of the present invention is very advantageous in terms of safety and cost.

The amount of a metal catalyst selected from the group consisting of tungstic acid, heterotungstic acid, and salts thereof would vary depending on the type of catalyst or unsaturated triacyl glycerol serving as a substrate. It is not particularly limited. However, it is generally 0.1 to 30 moles, preferably 1 to 20 moles, and further preferably 5 to 15 moles relative to 100 moles of a substrate. More specifically, in a case in which $Na_2WO_4$ is used, the amount of the catalyst relative to 100 moles of a substrate is 1 to 30 moles, preferably 2 to 30 moles, and further preferably 5 to 15 moles. In addition, in a case in which $H_3(PW_{12}O_{40}).H_2O$ is used, the amount of the catalyst relative to 100 moles of a substrate is 0.1 to 10 moles and preferably 1 to 3 moles.

Also, the amount of the quaternary ammonium polybasic acid hydrogen salt used as a phase transfer catalyst is not particularly limited. However, it is generally 1 to 30 moles and preferably 5 to 15 moles relative to 100 moles of a substrate.

A particularly preferable reaction solvent is water. However, an organic solvent such as halogenated hydrocarbon (e.g., chloroform, dichloroethane, or methylene chloride), alcohol with a carbon number of 1 to 5, tetrahydrofuran, dioxane, acetonitrile, and the like may be used alone or in combinations of two or more.

The reaction temperature can range from room temperature to reflux temperature. In addition, the reaction time is generally approximately 1 to 24 hours, although it would vary depending on the reaction temperature or reactivity. Further, it is preferable to carry out a reaction with the addition of acid such as phosphoric acid or sulfuric acid. In addition, according to the method of the present invention, it has been found that a reaction sufficiently proceeds even at a reaction temperature of 90° C. for a reaction time of less than 10 hours or even less than 5 hours. In the case of a conventional method for producing carboxylic acid (JP Patent Publication (Kokai) No. 5-4938 A (1993)), it is necessary to carry out a reaction at 100° C. for 10 to 24 hours. Therefore, according to the present invention, carboxylic acid can be obtained with high efficiency.

After the completion of reaction, monocarboxylic acid, dicarboxylic acid, and tricarboxylic acid generated from a reaction mixture are isolated according to need. Preferably, monocarboxylic acid is obtained from a reaction mixture via extraction separation with the use of a nonaqueous solvent. Examples of nonaqueous solvents include ethyl acetate and aliphatic hydrocarbon solvents such as pentane, hexane, heptane, octane, and nonane.

Next, the pH of an aqueous phase containing dicarboxylic acid and tricarboxylic acid is adequately adjusted, followed by extraction of dicarboxylic acid with the addition of a nonaqueous solvent. Further, nonaqueous solvent is added to a remaining reaction mixture for extraction of tricarboxylic acid. Alternatively, tricarboxylic acid may be precipitated via recrystallization from the aqueous phase to which tricarboxylic acid has been extracted.

In addition, for instance, a conventionally known purification means such as chromatography or distillation may be used instead of extraction separation described above or in combination with extraction separation.

According to the production method of the present invention, monocarboxylic acid, dicarboxylic acid, and/or tricarboxylic acid, which correspond to unsaturated triacyl glycerol used as a starting material, can be produced by an efficient and simplified method. According to the method of the present invention, dicarboxylic acids such as adipic acid, azelaic acid, sebacic acid, succinic acid, glutaric acid, undecanedioic acid, tridecanoic acid, and suberic acid can be produced, for example. In addition, tricarboxylic acid such as triazelain can be produced. For example, dicarboxylic acid and tricarboxylic acid obtained by the method of the present invention can be widely used as starting materials for polyester-based plasticizers, nylons, polyester starting materials, lubricating oil, and the like.

EXAMPLES

The present invention is hereafter described in greater detail with reference to the following examples, although the technical scope of the present invention is not limited thereto.

Example 1

Oxidation reaction was carried out with the use of a catalyst system containing 30% hydrogen peroxide water (oxidant) (13.2 equivalents), sodium tungstate and hydrogen sulfate methyltrioctylammonium (0.15 equivalents each), sulfuric acid (0.37 mmol), and distilled water (1 ml) for triolein (1.0 g). As a result, the yield of nonanoic acid, which is monocarboxylic acid, was 87%. In addition, the yield of azelaic acid was 19%. The remaining product was triazelain when the reaction was terminated. Accordingly, it has been revealed that an oxidation reaction of triolein with hydrogen peroxide is a selective reaction, and that a reaction in which oxidation cleavage of an olefin portion results in generation of carboxylic acid proceeds in a preferential manner. The reaction formula is shown below.

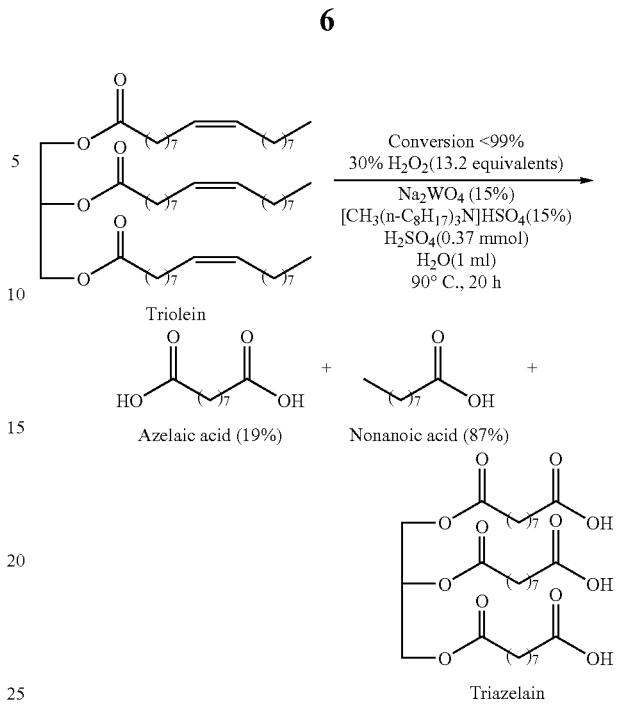

Example 2

Next, oxidation reaction was carried out using carrot oil as unsaturated triacyl glycerol. Carrot oil is a mixture of several different compounds. Therefore, the accurate molecular weight thereof is unknown. However, petroselinic acid- and oleic acid-derived components account for 80% of the total composition. These components are different from each other only in terms of the position of an introduced double bond and identical to each other in terms of the molecular weight. Therefore, the molecular weight of carrot oil was assumed to be equivalent to that of triolein. The amounts of catalysts used were the same as those used in Example 1.

Oxidation reaction was carried out with the use of a catalyst system containing 30% hydrogen peroxide water (oxidant) (13.2 equivalents), sodium tungstate and hydrogen sulfate methyltrioctylammonium (0.15 equivalents each), sulfuric acid (0.37 mmol), and distilled water (1 ml) for carrot oil (1.0 g). The reaction proceeded under conditions that were the same as those for the triolein oxidation reaction in Example 1. The conversion reached 99% or more in 20 hours. The yield of adipic acid was 14%, that of azelaic acid was 35%, that of lauric acid was 22%, and that of nonanoic acid was 31%.

Example 3

Oxidation reaction was carried out with the use of a catalyst system containing 30% hydrogen peroxide water (oxidant) (13.2 equivalents), phosphosodium tungstate $Na(PW_{12}O_{40})$ ·$nH_2O$ and hydrogen sulfate methyltrioctylammonium (0.05 equivalents each), a 40% phosphoric acid aqueous solution (corresponding to 0.5 mmol of phosphoric acid) for triolein (1.0 g). As a result, the yield of nonanoic acid (monocarboxylic acid) was 69%. In addition, the yield of azelaic acid was 52%. The remaining product was triazelain when the reaction was terminated.

All of the publications, patents, and patent applications are incorporated by reference herein in their entirety.

What is claimed is:

1. A method for producing monocarboxylic acid, dicarboxylic acid and tricarboxylic acid, comprising allowing unsaturated triacyl glycerol to react with hydrogen peroxide in the presence of a quaternary ammonium polybasic acid hydrogen salt and at least one member selected from the group consisting of tungstic acid, heterotungstic acid, and salts thereof.

2. The method for producing monocarboxylic acid, dicarboxylic acid and tricarboxylic acid according to claim 1, wherein unsaturated triacyl glycerol is triolein or carrot oil.

3. The method for producing monocarboxylic acid, dicarboxylic acid and tricarboxylic acid according to claim 1, wherein at least one member selected from the group consisting of tungstic acid, heterotungstic acid, and salts thereof is sodium tungstate.

4. The method for producing monocarboxylic acid, dicarboxylic acid and tricarboxylic acid according to claim 2, wherein at least one member selected from the group consisting of tungstic acid, heterotungstic acid, and salts thereof is sodium tungstate.

5. The method for producing monocarboxylic acid, dicarboxylic acid and tricarboxylic acid according to claim 1, wherein at least one member selected from the group consisting of tungstic acid, heterotungstic acid, and salts thereof is phosphosodium tungstate.

6. The method for producing monocarboxylic acid, dicarboxylic acid and tricarboxylic acid according to claim 2, wherein at least one member selected from the group consisting of tungstic acid, heterotungstic acid, and salts thereof is phosphosodium tungstate.

7. The method for producing monocarboxylic acid, dicarboxylic acid and tricarboxylic acid according to claim 1, wherein the quaternary ammonium polybasic acid hydrogen salt is hydrogen sulfate methyltrioctyl ammonium.

* * * * *